(12) United States Patent
Miyagawa et al.

(10) Patent No.: US 11,529,165 B2
(45) Date of Patent: Dec. 20, 2022

(54) CATHETER

(71) Applicant: Nipro Corporation, Osaka (JP)

(72) Inventors: Katsuya Miyagawa, Osaka (JP); Misa Matsumoto, Osaka (JP); Tomonori Nakamura, Osaka (JP)

(73) Assignee: Nipro Corporation, Osaka (JP)

( * ) Notice: Subject to any disclaimer, the term of this patent is extended or adjusted under 35 U.S.C. 154(b) by 713 days.

(21) Appl. No.: 16/530,615

(22) Filed: Aug. 2, 2019

(65) Prior Publication Data

US 2019/0365413 A1    Dec. 5, 2019

Related U.S. Application Data

(63) Continuation of application No. 15/116,562, filed as application No. PCT/JP2015/053101 on Feb. 4, 2015, now Pat. No. 10,405,881.

(30) Foreign Application Priority Data

Feb. 6, 2014  (JP) .............................. JP2014-020927
May 20, 2014  (JP) .............................. JP2014-104489

(51) Int. Cl.
*A61B 17/3207* (2006.01)
*A61B 8/12* (2006.01)
(Continued)

(52) U.S. Cl.
CPC ........ *A61B 17/320783* (2013.01); *A61B 8/12* (2013.01); *A61B 8/445* (2013.01);
(Continued)

(58) Field of Classification Search
CPC ........ A61B 17/3207; A61B 17/320783; A61B 17/320758; A61B 2017/22069;
(Continued)

(56) References Cited

U.S. PATENT DOCUMENTS 4,794,931 A    1/1989  Yock
5,190,046 A    3/1993  Shturman
(Continued)

FOREIGN PATENT DOCUMENTS

CN    1049287 A    2/1991
CN    1705461 A    12/2005
(Continued)

OTHER PUBLICATIONS

Third Notice of Reasons for Refusal dated May 7, 2019 issued in Chinese Patent Application No. 201580007589.0 (8 pages).
(Continued)

*Primary Examiner* — Ashley L Fishback
(74) *Attorney, Agent, or Firm* — Rothwell, Figg, Ernst & Manbeck, P.C.

(57) ABSTRACT

To provide a catheter having a simple structure capable of excising an atheroma in a blood vessel and capable of obtaining ultrasonic images of a blood vessel.
[Solution] A catheter 10 has a shaft 11 having an opening 20 in a part of the side wall on the distal end side, a cutter 12 which is located in the vicinity of the opening 20 in the internal space of the shaft 11 and which can move in the axial direction 101 of the shaft 11, a balloon 23 which is disposed on the side opposite to the opening 20 with respect to the axis of the shaft 11 and which outwardly expands from the side wall of the shaft 11, and a phased array ultrasound probe 17 disposed along the circumferential direction 102 of the outer peripheral surface of the side wall in the vicinity of the opening 20 at least on the same side as the side where the opening 20 is provided with respect to the axis of the shaft 11.

3 Claims, 11 Drawing Sheets

(51) Int. Cl.
  *A61B 8/00* (2006.01)
  *A61B 17/22* (2006.01)
  *A61B 90/00* (2016.01)
(52) U.S. Cl.
  CPC ............... *A61B 17/320758* (2013.01); *A61B 2017/22069* (2013.01); *A61B 2017/22071* (2013.01); *A61B 2017/320716* (2013.01); *A61B 2090/3735* (2016.02); *A61B 2090/3784* (2016.02)
(58) Field of Classification Search
  CPC ........... A61B 2017/320716; A61B 2090/3735; A61B 2090/3784
  See application file for complete search history.

(56) References Cited

U.S. PATENT DOCUMENTS

| | | | |
|---|---|---|---|
| 5,383,460 | A | 1/1995 | Jang et al. |
| 5,429,136 | A | 7/1995 | Milo et al. |
| 7,753,852 | B2 | 7/2010 | Maschke |
| 7,944,568 | B2 | 5/2011 | Teramura et al. |
| 2004/0068191 | A1 | 4/2004 | Seward et al. |
| 2004/0158143 | A1 | 8/2004 | Flaherty et al. |
| 2005/0187571 | A1 | 8/2005 | Maschke |
| 2005/0203553 | A1 | 9/2005 | Maschke |
| 2006/0135870 | A1 | 6/2006 | Webler |
| 2007/0191812 | A1 | 8/2007 | Nishide et al. |
| 2012/0123352 | A1 | 5/2012 | Fruland et al. |
| 2012/0253186 | A1 | 10/2012 | Simpson et al. |
| 2013/0245430 | A1 | 9/2013 | Selmon et al. |
| 2015/0141816 | A1 | 5/2015 | Gupta |
| 2015/0164423 | A1 | 6/2015 | Webler |

FOREIGN PATENT DOCUMENTS

| | | | |
|---|---|---|---|
| CN | 1893997 | A | 1/2007 |
| CN | 102198305 | A | 9/2011 |
| CN | 102460118 | A | 5/2012 |
| CN | 103037795 | A | 4/2013 |
| CN | 103252011 | A | 8/2013 |
| CN | 103281964 | A | 9/2013 |
| EP | 1 568 324 | A2 | 8/2005 |
| JP | S62270140 | A | 11/1987 |
| JP | H04-12742 | A | 1/1992 |
| JP | H05-56984 | A | 3/1993 |
| JP | H06-30943 | A | 2/1994 |
| JP | H08508895 | A | 9/1996 |
| JP | H09182754 | A | 7/1997 |
| JP | 11056752 | A | 3/1999 |
| JP | 2000-329534 | A | 11/2000 |
| JP | 2002-509768 | A | 4/2002 |
| JP | 2005230550 | A | 9/2005 |
| JP | 2008-523954 | A | 7/2008 |
| JP | 2014505496 | A | 3/2014 |
| WO | 9407418 | A1 | 4/1994 |
| WO | 1995/019143 | A1 | 7/1995 |
| WO | 99/49910 | A2 | 10/1999 |
| WO | 01/15609 | A1 | 3/2001 |
| WO | 2012064966 | A2 | 5/2012 |
| WO | 2013/012841 | A1 | 1/2013 |
| WO | 2013/172970 | A1 | 11/2013 |

OTHER PUBLICATIONS

International Search Report, with English version, issued in International Patent Application No. PCT/JP2015/053101, 7 pages (dated Mar. 31, 2015).
Written Opinion issued (in Japanese) in International Patent Application No. PCT/JP2015/053101, 5 pages (dated Mar. 31, 2015).
International Preliminary Report on Patentability, with English version, issued in International Patent Application No. PCT/JP2015/053101, 14 pages (dated Aug. 18, 2016).
Supplementary Partial Search Report issued in European Patent Application No. 15746921.4, 3 pages (dated Aug. 30, 2017).
Supplementary European Search Report issued in European Patent Application No. 15746921.4, 11 pages (dated Nov. 20, 2017).
Japanese Office Action issued in related Japanese Patent Application No. 2014-104489 dated Nov. 7, 2017.
Japanese Office Action issued in related Japanese Patent Application No. 2014-020927 dated Oct. 10, 2017.
Japanese Office Action issued in related Japanese Patent Application No. 2014-104489 dated Feb. 20, 2018.
Japanese Office Action dated Aug. 28, 2018 issued in Japanese Patent Application No. 2017-233976. (4 pages).
Chinese Office Action dated in Jun. 24, 2021 in Chinese Patent Application No. 201911156042 (10 pages).
European communication pursuant to Article 94(3) EPC dated Nov. 27, 2019 issued in European Application No. 15 746 921.4. (4 pages).

CATHETER

CROSS-REFERENCE TO RELATED APPLICATION

This application claims the benefit under 35 U.S.C. § 120 of the filing date of non-provisional U.S. patent application Ser. No. 15/116,562, filed Aug. 4, 2016, which is a 35 U.S.C. 371 National Phase Entry Application from PCT/JP2015/053101, filed Feb. 4, 2015, which claims the benefit under 35 U.S.C. § 119(a) of the filing date of Japanese Patent Application No. 2014-020927, filed Feb. 6, 2014, and Japanese Patent Application No. 2014-104489, filed May 20, 2014, the respective disclosure(s) which is(are) incorporated herein by reference.

TECHNICAL FIELD

The present invention relates to a catheter to be inserted into a blood vessel in order to excise an atheroma adhering to the inner wall of a blood vessel.

BACKGROUND ART

Heretofore, medical treatment of inserting a catheter into a blood vessel to excise an atheroma generated in the blood vessel has been performed. An analysis of whether or not an atheroma is generated in a blood vessel has been performed by inserting a catheter having an ultrasound probe into the blood vessel to obtain an ultrasonic image. Moreover, for the analysis of whether or not an atheroma is present in a blood vessel, image analysis by an optical coherence tomography (hereinafter also referred to as "OCT".), for example, can be conducted (Patent Literature 4).

In order to excise an atheroma found in a blood vessel, an atheroma excision catheter has been used which excises an atheroma with a cutter through an opening in the side wall. The atheroma excision catheter is inserted into a blood vessel to the position where an opening faces the atheroma, and then a balloon provided in the vicinity of the opening is expanded, so that the opening is brought close to the atheroma, so that the atheroma enters a lumen of the atheroma excision catheter through the opening. In the lumen of the atheroma excision catheter, a cutter is movably provided in the axial direction. The cutter receives drive transmitted from a motor to be rotated in the lumen. The cutter is moved in the lumen while being rotated to thereby excise the atheroma entering the lumen. The excised atheroma is accommodated in the lumen of the atheroma excision catheter (Patent Literatures 1 and 2).

In the excision of the atheroma described above, ultrasonic images are obtained immediately before the excision in order to align the positions of the atheroma and the opening of the atheroma excision catheter. Thereafter, the atheroma is excised by the atheroma excision catheter. Furthermore, ultrasonic images are obtained again in order to check the state of the blood vessel after the excision of the atheroma. When it is temporarily judged that the atheroma is not sufficiently excised, the remaining atheroma is excised again by the atheroma excision catheter, and thereafter the state of the blood vessel is checked again. In such an operation, the catheter having the ultrasound probe and the atheroma excision catheter are alternately inserted into the blood vessel, which is likely to complicate the operation. In view of such circumstances, a catheter has been devised in which an atheroma excision catheter is provided with an ultrasound probe capable of rotating around the axis (Patent Literature 3).

CITATION LIST

Patent Literature

[Patent Literature 1] Japanese Unexamined Patent Publication Application No. 6-30943
[Patent Literature 2] Japanese Unexamined Patent Publication Application No. 5-56984
[Patent Literature 3] Japanese Unexamined Patent Application Publication (Translation of
[Patent Literature 4] Japanese Unexamined Patent Application Publication (Translation of PCT Application) No. 2008-523954

SUMMARY OF INVENTION

Technical Problems

The atheroma excision catheter provided with an ultrasound probe described above has problems that the attachment structure of the cutter and the ultrasound probe and a structure for rotating each of the cutter and the ultrasound probe are complicated, the catheter size increases, and instability of the operation due to failures and the like increases.

In the excision of the atheroma described above, in order to align the positions of the atheroma and the opening of the atheroma excision catheter, image analysis by the OCT is conducted before the excision, and thereafter, the atheroma is excised by the atheroma excision catheter. Furthermore, image analysis by the OCT is conducted again in order to check the state of the blood vessel after the excision of the atheroma. When it is temporarily judged that the atheroma is not sufficiently excised, the remaining atheroma is excised again by the atheroma excision catheter, and thereafter the state of the blood vessel is checked again. In such an operation, the catheter for the OCT and the atheroma excision catheter are alternately inserted into the blood vessel, which is likely to complicate the operation.

The present invention has been made in view of such circumstances. It is an object of the present invention to provide a catheter having a simple structure capable of excising an atheroma in a blood vessel and capable of obtaining ultrasonic images of the blood vessel.

It is another object of the present invention to provide a catheter having a simple structure capable of excising an atheroma in a blood vessel and capable of obtaining images of the blood vessel by the OCT.

Solution to Problems (1) A catheter according to the present invention has a tube body having an opening in a part of the side wall on the distal end side, a cutter which is located in the vicinity of the opening in the internal space of the tube body and which can move in the axial direction of the tube body, a balloon which is disposed on a side opposite to the opening with respect to the axis of the tube body and which outwardly expands from the side wall of the tube body, and a phased array ultrasound probe disposed along the circumferential direction of the outer peripheral surface of the side wall in the vicinity of the opening at least on the same side as the side where the opening is provided with respect to the axis of the tube body.

The catheter is inserted into a blood vessel from the distal end side. Due to the fact that the balloon is expanded in a state where the opening of the tube body is aligned with an atheroma in the blood vessel, the tube body is fixed to the blood vessel, so that the atheroma enters the internal space of the tube body from the opening. By the cutter moved in the axial direction of the tube body, the atheroma entering the internal space of the tube body is excised. By the ultrasound probe disposed in the vicinity of the opening of the tube body, ultrasonic images of the excised atheroma are obtained.

(2) The catheter further has an outer tube body which is provided on the outside of the tube body and which can relatively move in the axial direction with respect to the tube body, in which the ultrasound probe may be provided on the outer tube body.

Since the ultrasound probe can move in the blood vessel in connection with the relative movement of the outer tube body, ultrasonic images of cross sections or partial cross sections of the blood vessel different in the position in the length direction can be obtained by moving the ultrasound probe with respect to the atheroma.

(3) The outer tube body has a notch portion in which a part corresponding to the balloon is cut out, and a support portion which is disposed on a side opposite to the notch portion with respect to the axis of the outer tube body and which can be moved to a first position where the support portion covers the opening and a second position where the support portion opens the opening by the relative movement, in which the ultrasound probe is provided on the support portion and the notch portion may not abut on the balloon in the state of being outwardly expanded at the first position.

Even when the outer tube body is relatively moved to the first position where the outer tube body is overlapped with the opening in the state where the balloon is expanded, the outer tube body and the balloon do not interfere with each other by the notch portion. In the support portion at the first position, the atheroma located at a position corresponding to the opening and the ultrasound probe face each other, so that ultrasonic images of the atheroma can be obtained.

(4) The ultrasound probe may be fixed on the distal end side relative to the opening in the tube body.

(5) The ultrasound probe may be fixed on the proximal end side relative to the opening in the tube body.

(6) A catheter according to the present invention has a tube body having an opening in a part of the side wall on the distal end side, a cutter which is located in the vicinity of the opening in the internal space of the tube body and which can move in the axial direction of the tube body, a torque shaft which is inserted into and passed through the internal space of the tube body and is connected to the cutter in such a manner as to be able to transmit a rotation torque to the cutter, a light guide material provided along the torque shaft, a reflective material which reflects light emitted from the light guide material in a second direction crossing a first direction in which the light guide material is extended, and a balloon which is disposed on a side opposite to the opening with respect to the axis of the tube body and outwardly expands from the side wall of the tube body.

The catheter is inserted into a blood vessel from the distal end side. Due to the fact that the balloon is expanded in a state where the opening of the tube body is aligned with an atheroma in the blood vessel, the tube body is fixed to the blood vessel, so that the atheroma enters the internal space of the tube body from the opening. By the cutter moved in the axial direction of the tube body, the atheroma entering the internal space of the tube body is excised. Light emitted from the light guide material provided along the torque shaft is reflected by the reflective material to be emitted to the blood vessel. Due to the fact that the reflected light from the blood vessel is treated as an interference signal by an OCT system through the reflective material and the light guide material, images of the blood vessel in the vicinity of the atheroma are obtained.

(7) Preferably, the light guide material and the reflective material are disposed in the internal space of the torque shaft and the reflective material emits light reflected in the second direction to the outside of the torque shaft through the opening formed in the side wall of the torque shaft.

Thus, light can be guided to be reflected in the torque shaft.

(8) Preferably, the light guide material and the reflective material can be rotated integrally with the torque shaft.

Thus, the excision of an atheroma and the OCT can be realized by controlling the number of rotations of a rotating device, such as a motor, connected to the torque shaft.

(9) Preferably, the light guide material and the reflective material can move integrally with the torque shaft along the first direction.

Thus, images of a blood vessel can be obtained along the first direction.

(10) Preferably, the light guide material and the reflective material are disposed in the internal space of the torque shaft.

Thus, the light guide material and the reflective material are covered with the torque shaft to be protected, and therefore the light guide material and the reflective material are hard to be damaged.

(11) Preferably, the light guide material and the reflective material are disposed on the outer peripheral surface side of the torque shaft.

Thus, even when a guide wire is inserted into and passed through the internal space of the torque shaft, light reflected from the reflective material is not blocked by the guide wire.

(12) Preferably, a guide wire lumen is provided along the tube body.

Thus, the catheter can be inserted into a blood vessel along the guide wire.

Advantageous Effects of Invention

According to the catheter of the present invention, an atheroma in a blood vessel can be excised and ultrasonic images of the blood vessel can be obtained by a simple structure.

Moreover, according to the catheter of the present invention, an atheroma in a blood vessel can be excised and images of the blood vessel by the OCT can be obtained by a simple structure.

DESCRIPTION OF EMBODIMENTS

Hereinafter, preferable embodiments of the present invention are described. It is a matter of course that the embodiments merely describe one embodiment of the present invention and the embodiments can be altered insofar as the scope of the present invention is not altered.

First Embodiment

Figure 1:
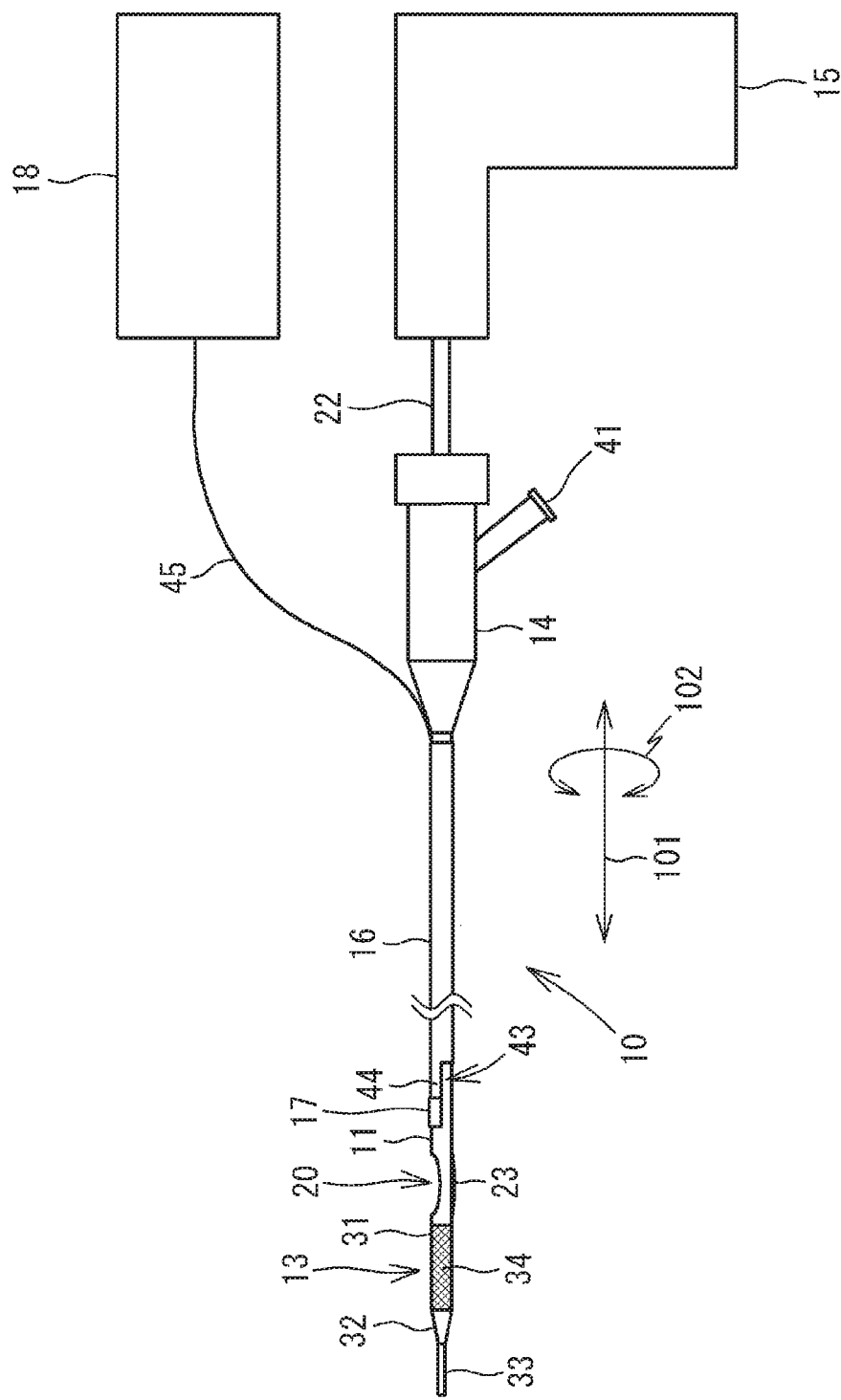
FIG. 1 is a view illustrating the external configuration of a catheter 10 in a state where a balloon 23 is contracted.
Figure 2:
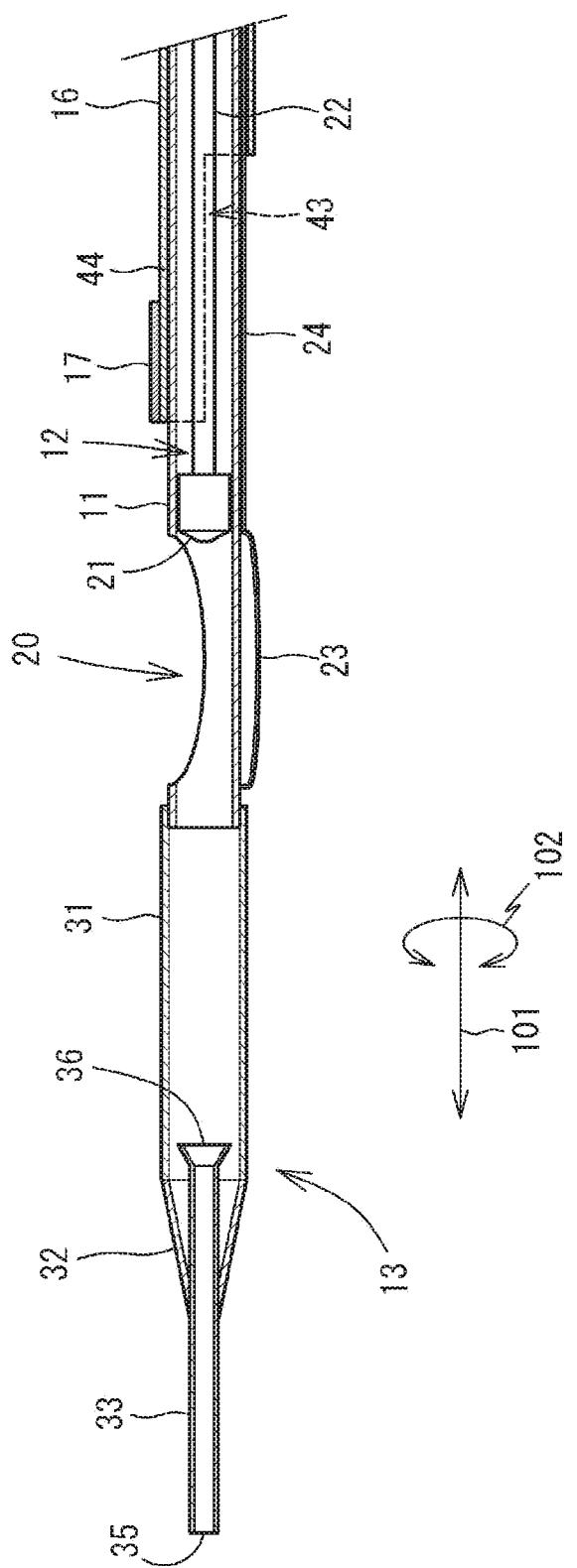
FIG. 2 is an enlarged cross sectional view illustrating the internal configuration in the vicinity of a distal end portion 13 of the catheter 10.

As illustrated in FIGS. 1 and 2, a catheter 10 has a shaft 11, a cutter 12 provided in the shaft 11, a distal end portion 13 configuring the distal end of the shaft 11, a proximal end portion 14 connected to the proximal end of the shaft 11, an actuator 15 which gives rotary drive to the cutter 12, an IVUS shaft 16, and an ultrasound probe 17 provided on the IVUS shaft 16. The catheter 10 is used as a medical instrument which is inserted into a blood vessel to excise an atheroma or photographs ultrasonic images of a blood vessel.

The shaft 11 is a tube capable of containing the cutter 12 thereinside. The shaft 11 is configured from a surgical stainless steel circular tube or a synthetic resin circular tube, for example, and has flexibility which allows the shaft 11 to be elastically curved corresponding to the curved shape of a blood vessel. The distal end and the proximal end of the shaft 11 each are opened. The outer diameter of the shaft 11 is set according to the inner diameter of a blood vessel into which the shaft 11 is to be inserted, e.g., coronary arteries. The inner diameter of the shaft 11 is set according to the outer diameter of the cutter 12. The outer diameter and the inner diameter of the shaft 11 are almost uniform over the axial direction 101 of the shaft 11. The length in the axial direction 101 of the shaft 11 is set in consideration of the length from catheter insertion portions, such as the human limbs, to the affected portion.

As illustrated in FIG. 2, an opening 20 is formed in the vicinity of the distal end portion 13 in the shaft 11. The opening 20 is formed by cutting out a part of the side wall of the shaft 11. The shape and the size of the opening 20 are set in consideration of the shape and the size of an atheroma which is probably formed in the affected portion. The shaft 11 is equivalent to the tube body.

As illustrated in FIG. 2, the cutter 12 is provided in the vicinity of the opening 20 in the internal space of the shaft 11. The cutter 12 has a cutting portion 21 and a shaft 22. The cutting portion 21 has an approximately cylindrical shape and the outer diameter is a little smaller than the inner diameter of the shaft 11. On the distal end side of the cutting portion 21, a plurality of blades are formed in such a manner as to radially extend from the center. Although not illustrated in FIG. 2, a through-hole is formed along the axial direction 101 in the center of the cutting portion 21. The shaft 22 is extended from the proximal end of the cutting portion 21 to the outside of the proximal end portion 14. The shaft 22 is a long and narrow tube and the internal space communicates with the through-hole of the cutting portion 21. The internal space of the shaft 22 and the through-hole of the cutting portion 21 are configured so that a guide wire is inserted into and passed through the internal space and the through-hole.

As illustrated in FIG. 1, the shaft 22 is connected to the actuator 15. Due to the fact that the shaft 22 receives drive transmitted from the actuator 15 to rotate, the cutting portion 21 rotates. Due to the fact that the shaft 22 is moved in the axial direction 101, the cutting portion 21 moves in the axial direction 101 in the internal space of the shaft 11.

As illustrated in FIGS. 1 and 2, a balloon 23 is provided at a position opposite to the opening 20 with respect to the axis of the shaft 11. The balloon 23 can outwardly expand from the side wall of the shaft 11 and is folded and stuck to the side wall of the shaft 11 until the catheter 10 is inserted into a blood vessel. As raw materials of the balloon 23, materials having biocompatibility are preferable. Specific examples of the materials include polyurethane, polyethylene, polyester, polypropylene, polyamide, polyamide elastomer, polytetrafluoroethylene, polyvinylidene fluoride, and the like.

As illustrated in FIG. 2, the proximal end side of the balloon 23 is connected to a tube body for balloon 24 provided along the side wall of the shaft 11. The internal space of the tube body for balloon 24 is caused to communicate with the internal space of the balloon 23. The tube body for balloon 24 is extended to the proximal end portion 14 and the internal space of the tube body for balloon 24 is connected to a port 41 of the proximal end portion 14. Due to the fact that liquid, such as physiological saline, injected from the port 41 of the proximal end portion 14 flows into the balloon 23, the balloon 23 is expanded in a blood vessel. The tube body for balloon 24 is a molded body of flexible plastic which can be elastically deformed, such as polyamide, polyamide elastomer, and polyetheramide.

As illustrated in FIGS. 1 and 2, the distal end portion 13 is connected to the distal end of the shaft 11. As illustrated in FIG. 2, the distal end portion 13 has a blade tube 31, a reduced diameter portion 32, and a distal end tip 33.

As illustrated in FIGS. 1 and 2, the blade tube 31 is a circular tube in which both sides are opened. The blade tube 31 is connected to the distal end of the shaft 11 and the internal space thereof is caused to communicate with the internal space of the shaft 11. The blade tube 31 is one in which flexible plastic which can be elastically deformed, such as polyamide, polyamide elastomer, and polyetheramide, is reinforced with a core material 34. The core material 34 is embedded in the side wall of the blade tube 31. The core material 34 is formed into a cylindrical shape by braiding wire rods, such as surgical stainless steel, into a mesh. The inner diameter of the blade tube 31 is almost equal to the outer diameter of the shaft 11 and the blade tube 31 is fitted to the distal end of the shaft 11 from the outside. The outer diameter and the inner diameter of the blade tube 31 are almost uniform over the axial direction 101. In each figure other than FIG. 1, the core material 34 is not illustrated.

As illustrated in FIGS. 1 and 2, the reduced diameter portion 32 is a circular tube in which both sides are opened and the outer diameter decreases in a tapered shape. The reduced diameter portion 32 is connected to the distal end of the blade tube 31 and the internal space thereof is caused to communicate with the internal space of the blade tube 31. The reduced diameter portion 32 contains flexible plastic which can be elastically deformed, such as polyamide and polyetheramide. The inner diameter on the proximal end side of the reduced diameter portion 32 is almost equal to the outer diameter of the distal end of the blade tube 31. The reduced diameter portion 32 is fitted to the distal end of the blade tube 31 from the outside, and then thermally fused thereto. The inner diameter on the distal end side of the reduced diameter portion 32 is almost equal to the outer diameter of the central portion of the distal end tip 33. On the distal end side of the reduced diameter portion 32, the thickness decreases toward the distal end side.

As illustrated in FIGS. 1 and 2, the distal end tip 33 is a circular tube in which both sides are opened and the outer diameter on a proximal end 36 side increases in a tapered shape. The distal end tip 33 is connected to the distal end of the reduced diameter portion 32 and the internal space thereof is caused to communicate with the internal space of the reduced diameter portion 32. The distal end 35 of the distal end tip 33 is projected from the distal end of the reduced diameter portion 32 to the outside in the axial direction 101. The proximal end 36 side of the distal end tip 33 is extended in the axial direction 101 in the internal space of the reduced diameter portion 32 and the proximal end 36 reaches the internal space of the blade tube 31. More specifically, a portion including a distal end side portion of the blade tube 31 and the reduced diameter portion 32 has a double tube structure in which the blade tube 31 and the reduced diameter portion 32 serve as the outer side and the distal end tip 33 serves as the inner side.

Although the diameter of the distal end tip 33 is increased on the proximal end 36 side, the outer diameter and the inner diameter of the other portion are almost uniform. The outer diameter of the uniform portion is smaller than the inner diameter of the blade tube 31 and is almost equal to the inner diameter of the distal end of the reduced diameter portion 32. Although the diameter of the proximal end 36 side is increased, the maximum diameter is smaller than the inner diameter of the blade tube 31.

The distal end tip 33 contains flexible plastic which can be elastically deformed, such as polyamide and polyetheramide. The distal end tip 33 is inserted into the distal end of the reduced diameter portion 32, and then thermally fused thereto. On the distal end of the distal end tip 33, a marker which can be confirmed by X-rays or the like may be provided.

The proximal end portion 14 is provided on the proximal end of the shaft 11. The proximal end portion 14 is a cylindrical member having an internal space continuing to the internal space of the shaft 11. The proximal end portion 14 is a molded body of resin, such as polypropylene or ABS. The proximal end portion 14 may serve as a handle in an operation of inserting and removing the shaft 11 into/from a blood vessel.

The proximal end portion 14 is provided with the port 41 extended in a direction crossing the axial direction 101. Another device, such as a syringe, is connected to the port 41, and then fluid, such as physiological saline, which is flown in and out from the device, flows in and out of the tube body for balloon 24 from the proximal end portion 14. The proximal end portion 14 may be provided with another port continuing to the internal space of the shaft 11. Such a port is used for the purpose of, for example, collecting an excised atheroma entering the inside of the shaft 11.

From an opening on the proximal end side of the proximal end portion 14, the shaft 22 of the cutter 12 is extended. The actuator 15 is connected to the shaft 22. In the actuator 15, a motor, a battery, and the like are built. To the shaft 22, rotation of the motor of the actuator 15 is transmitted.

As illustrated in FIGS. 1 and 2, the IVUS shaft 16 is provided on the outside of the shaft 11. The IVUS shaft 16 is a tube which allows the insertion of the shaft 11 into the IVUS shaft 16 in such a manner that the shaft 11 can relatively move in the axial direction 101. The IVUS shaft 16 is configured from a surgical stainless steel circular tube or a synthetic resin circular tube, for example, and has flexibility which allows the IVUS shaft 16 to be elastically curved corresponding to the curved shape of a blood vessel. The distal end and the proximal end of the IVUS shaft 16 each are opened. The outer diameter of the IVUS shaft 16 is set according to the inner diameter of a blood vessel into which the IVUS shaft 16 is to be inserted, e.g., coronary arteries. The inner diameter of the IVUS shaft 16 is set according to the outer diameter of the shaft 11. The outer diameter and the inner diameter of the IVUS shaft 16 are almost uniform over the axial direction 101. The length in the axial direction 101 of the IVUS shaft 16 is a little shorter than the length in the axial direction 101 of the shaft 11. Therefore, in the state where the IVUS shaft 16 is moved to the proximal end side with respect to the shaft 11 until the IVUS shaft 16 abuts on the proximal end portion 14, a distal end side relative to the opening 20 of the shaft 11 is projected from the distal end of the IVUS shaft 16 to be exposed to the outside as illustrated in FIG. 1. The IVUS shaft 16 is equivalent to the outer tube body.

As illustrated in FIG. 2, a notch portion 43 extending to the proximal end side along the axial direction 101 is formed at a position on a side corresponding to the side of the balloon 23 of the shaft 11 in the distal end portion of the IVUS shaft 16. The length in the circumferential direction 102 of the notch portion 43 is longer than the length in the circumferential direction 102 of the balloon 23 and about the half in the circumferential direction 102 of the IVUS shaft 16 is cut out. The length in the axial direction 101 of the notch portion 43 is a length in which the notch portion 43 does not abut on the balloon 23 in the state (FIG. 4) where the distal end portion of the IVUS shaft 16 is relatively moved to the distal end side with respect to the shaft 11 to a position where the distal end portion of the IVUS shaft 16 covers the opening 20 and is almost equal to the length in the axial direction 101 of the opening 20.

A portion which is formed into an approximately half tube shape by the notch portion 43 of the distal end portion of the IVUS shaft 16 is a support portion 44 for the ultrasound probe 17. The support portion 44 is located on the same side as the side on which the opening 20 is provided of the shaft 11 in the circumferential direction 102. When the IVUS shaft 16 is moved to the distal end side of the shaft 11, the support portion 44 is located at a first position (FIG. 4) where the support portion 44 covers the opening 20. When the IVUS shaft 16 is moved to the proximal end side of the shaft 11, the support portion 44 is located at a second position (FIG. 3) where the support portion 44 opens the opening 20.

The ultrasound probe 17 is provided on the outside of the support portion 44. The ultrasound probe 17 is a so-called phased array type, in which a plurality of elements are arranged along the circumferential direction 102 on the outer peripheral surface of the support portion 44. The number of the elements is not particularly limited. However, when the elements are arranged corresponding to the number of the elements provided on the half of the circumference of the IVUS shaft 16, for example, 32 elements are arranged in the circumferential direction. When the elements are electrically ignited in order, tomographic images of a blood vessel around the ultrasound probe 17 are collected. A cable 45 is connected to the elements of the ultrasound probe 17. The cable 45 is inserted into and passed through the internal space of the IVUS shaft 16, extended to the outside from the proximal end, and then connected to the control device 18. The control device 18 is one which supplies electric power to the ultrasound probe 17 and forms tomographic images based on electric signals obtained from the ultrasound probe 17 and is a known control device for use in intravascular ultrasound (IVUS).

Although not illustrated in each figure, the IVUS shaft 16 may be provided with a fitting structure which regulates the movement in the circumferential direction in such a manner that the IVUS shaft 16 does not relatively rotate in the circumferential direction (around the axial direction 101) with respect to the shaft 11 and can relatively move only with respect to the axial direction 101. Due to the fact that the fitting structure or the like is provided, the position of the notch portion 43 of the IVUS shaft 16 and the position of the ultrasound probe 17 are not displaced with respect to the circumferential direction 102 of the shaft 11.

[Usage Directions for Catheter 10]

Hereinafter, the usage directions for the catheter 10 are described with reference to FIGS. 3 and 4.

The catheter 10 is used when excising an atheroma 51 formed in the inner wall of a blood vessel 50. The position of the atheroma 51 is confirmed by the IVUS or the like beforehand. The catheter 10 is inserted into the blood vessel 50 from the distal end portion 13 in the state (FIG. 1) where the balloon 23 is contracted. Although not illustrated in each figure, a guide wire is inserted into the blood vessel 50 beforehand in the insertion of the catheter 10 into the blood vessel 50. The insertion of the guide wire into the blood vessel 50 is performed by a known technique. The catheter 10 is inserted into the blood vessel 50 from the distal end portion 13 while inserting the guide wire, which is inserted into the blood vessel 50, into the internal space of the distal end tip 33 of the distal end portion 13, the internal space of the shaft 11, the through-hole of the cutting portion 21 of the cutter 12, and then the internal space of the shaft 22 in order.

The distal end portion 13 is advanced to the atheroma 51 in the blood vessel 50 while being elastically curved along the guide wire at a portion where the blood vessel 50 is curved, such as coronary arteries. When the distal end portion 13 reaches the atheroma 51, so that the opening 20 of the shaft 11 faces the atheroma 51, the insertion of the shaft 11 into the blood vessel 50 is ended. By moving the support portion 44 of the IVUS shaft 16 to the first position where the support portion 44 covers the opening 20, and then electrically igniting the ultrasound probe 17, tomographic images of the blood vessel 50 including the opening 20 are collected. By confirming the formed tomographic images of the blood vessel 50 by the control device 18, it can be confirmed that the opening 20 has reached a position corresponding to the position of the atheroma 51 and the state of the atheroma 51 can be confirmed. Thereafter, the guide wire is drawn out of the proximal end portion 14 side of the catheter 10. The actuator 15 is connected to the shaft 22 of the cutter 12.

Figure 3:
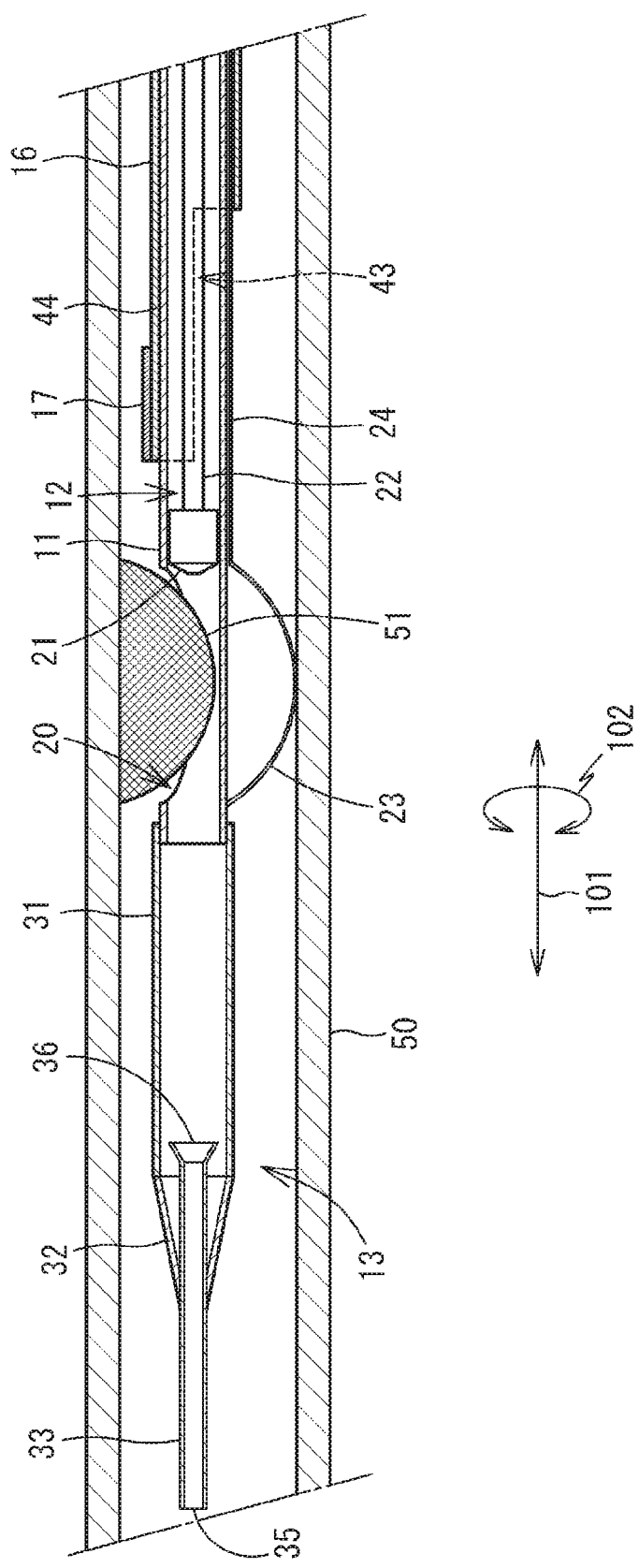
FIG. 3 is a schematic view illustrating a state where the balloon 23 is expanded in a blood vessel 50.
Figure 4:
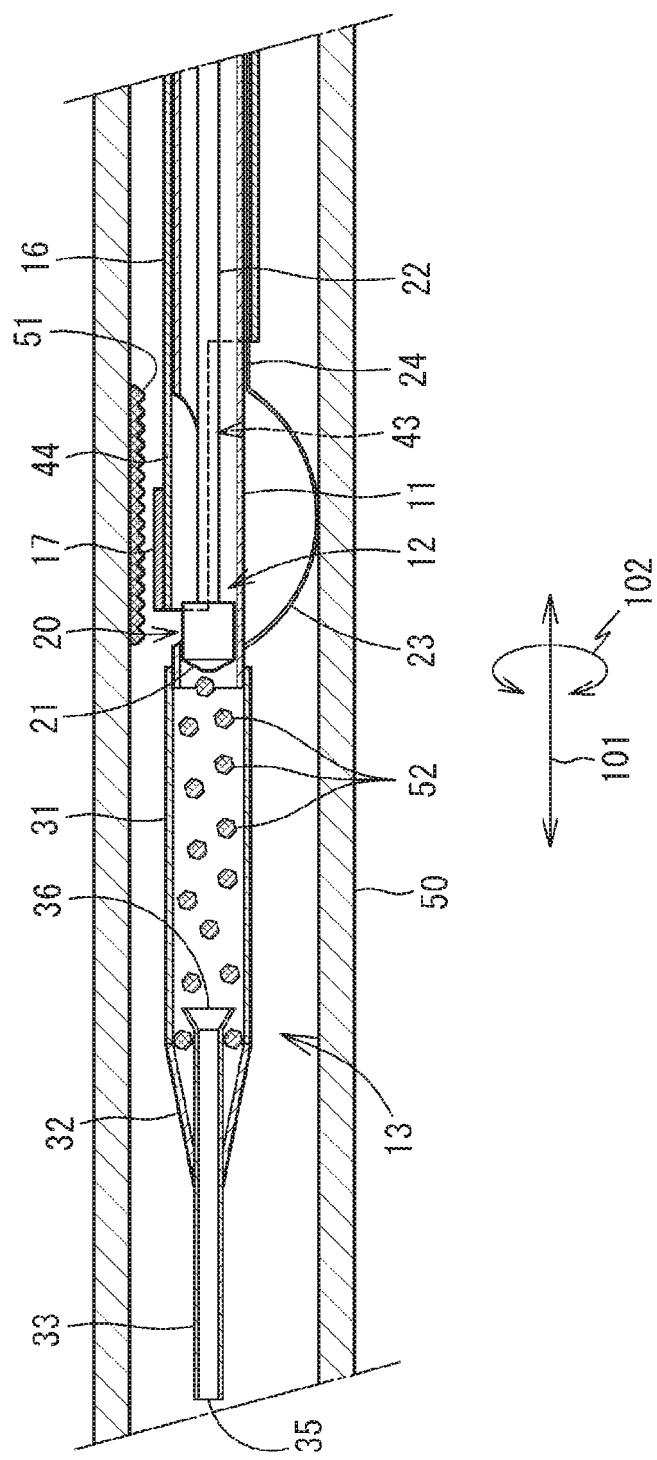
FIG. 4 is a schematic view illustrating a state where a support portion 44 is located at a first position after an atheroma 51 is excised in the blood vessel 50.

As illustrated in FIG. 3, in the state where the opening 20 of the shaft 11 faces the atheroma 51 and where the support portion 44 is located at the second position where the support portion 44 of the IVUS shaft 16 opens the opening 20, the balloon 23 in the contracted state is expanded by fluid which is caused to flow into the tube body for balloon 24 from the port 41. When the expanded balloon 23 abuts on the inner wall of the blood vessel 50 on a side opposite to the atheroma 51, the opening 20 is stuck to the atheroma 51, so that the atheroma 51 partially enters the internal space of the shaft 11 from the opening 20. In the state above, the catheter 10 is fixed to the blood vessel 50.

Subsequently, a motor of the actuator 15 is driven, so that the cutting portion 21 is rotated through the shaft 22 of the cutter 12. Due to the fact that the shaft 22 is advanced to the distal end side in the axial direction 10 with respect to the shaft 11 on the proximal end portion 14 side, the rotating cutting portion 21 abuts on the atheroma 51, so that the atheroma 51 is excised by the cutting portion 21. Fragments 52 of the excised atheroma 51 enter the internal space of the blade tube 31 through the internal space of the shaft 11.

After the atheroma 51 is excised by the cutter 12, the support portion 44 of the IVUS shaft 16 is located at the first position where the support portion 44 covers the opening 20. Then, the ultrasound probe 17 is electrically ignited, whereby tomographic images of the blood vessel 50 in the state where the atheroma 51 is excised are collected. Thus, the state where the atheroma 51 is excised can be immediately confirmed, i.e., without drawing out the catheter 10 from the blood vessel 50. Therefore, when the excision of the atheroma 51 is insufficient, for example, the support portion 44 of the IVUS shaft 16 is located at the second position again, and then the remaining atheroma 51 can be excised by the cutter 12. The collection of the tomographic images of the blood vessel 50 may be performed by electrically igniting the ultrasound probe 17 while moving the IVUS shaft 16 in the axial direction 101 with respect to the shaft 11. Thus, the tomographic images are continuously collected in the length direction (which is almost in agreement with the axial direction 101) of the blood vessel 50. Then, when the excision of the atheroma 51 is completed, the balloon 23 is contracted, and then the catheter 10 is drawn out of the blood vessel 50 to be collected.

Operational Effects of First Embodiment

According to the catheter 10 of the first embodiment, the atheroma 51 in the blood vessel 50 can be excised and the ultrasonic images of the blood vessel 50 can be obtained by the simple structure.

Moreover, since the IVUS shaft 16 can be relatively moved in the axial direction 101 with respect to the shaft 11 and the ultrasound probe 17 can be moved in the length direction (axial direction 101) in the blood vessel 50 in connection with the relative movement, the ultrasound probe 17 can be moved with respect to the atheroma 51, so that tomographic images different in the position in the length direction of the blood vessel 50 can be obtained.

Moreover, the notch portion 43 is provided in the IVUS shaft 16, and therefore even when the support portion 44 provided on the side opposite to the notch portion 43 is located at the first position where the support portion 44 covers the opening 20, the balloon 23 which is outwardly expanded and the IVUS shaft 16 do not abut on each other by the notch portion 43. Therefore, in the support portion 44 at the first position, tomographic images including the atheroma 51 at a position facing the opening 20 can be obtained.

Modification of First Embodiment

In the first embodiment described above, although the ultrasound probe 17 is provided in the IVUS shaft 16, the IVUS shaft 16 may not be provided and the ultrasound probe 17 may be provided on the outer peripheral surface of the shaft 11.

Figure 5:
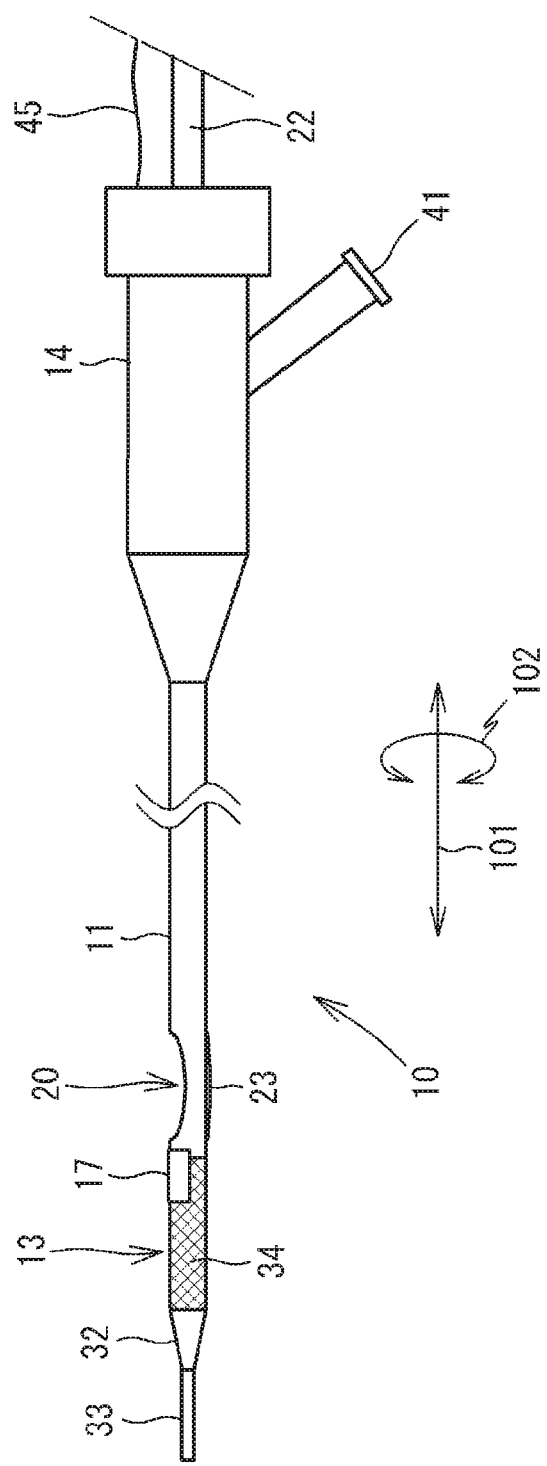
FIG. 5 is a view illustrating a modification of the catheter 10.
Figure 6:
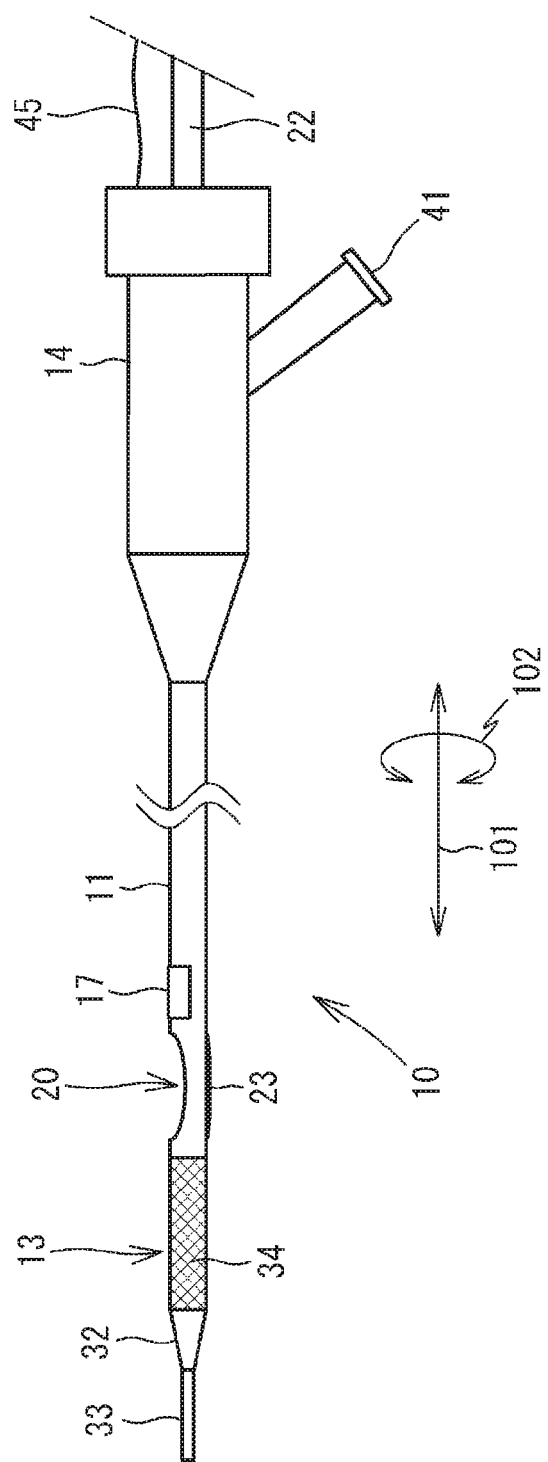
FIG. 6 is a view illustrating a modification of the catheter 10.

As illustrated in FIG. 5, the ultrasound probe 17 is provided in the vicinity of the opening 20 in the shaft 11 and is provided on the distal end side relative to the opening 20. In this modification, the ultrasound probe 17 and the balloon 23 are arranged in such a manner as not to interfere with each other, the ultrasound probe 17 may have 32 elements corresponding to the number of the elements provided on the half of the circumference of the shaft 11 as in the first embodiment described above or may have 64 elements corresponding to the number of the elements provided on the entire circumference of the shaft 11. Although not illustrated in FIG. 5, the cable 45 extended from the ultrasound probe 17 is inserted into and passed through the internal space of the shaft 11 to be connected to the control device 18. As illustrated in FIG. 6, the ultrasound probe 17 may be provided in the vicinity of the opening 20 in the shaft 11 and on the proximal end side relative to the opening 20.

Since the IVUS shaft 16 is not provided according to such a modification, a reduction in size, particularly a reduction in diameter, of the catheter 10 is achieved, and the structure becomes simpler. By deflating the balloon 23 and moving the ultrasound probe 17 in the length direction of the blood vessel 50 together with the catheter 10, tomographic images of the blood vessel 50 containing the atheroma 51 and tomographic images continuing in the length direction of the blood vessel 50 can be collected. Moreover, due to the fact that the ultrasound probe 17 is provided over the entire circumference of the shaft 11, tomographic images of the entire circumference of the blood vessel 50 can be collected.

Second Embodiment

Figure 7:
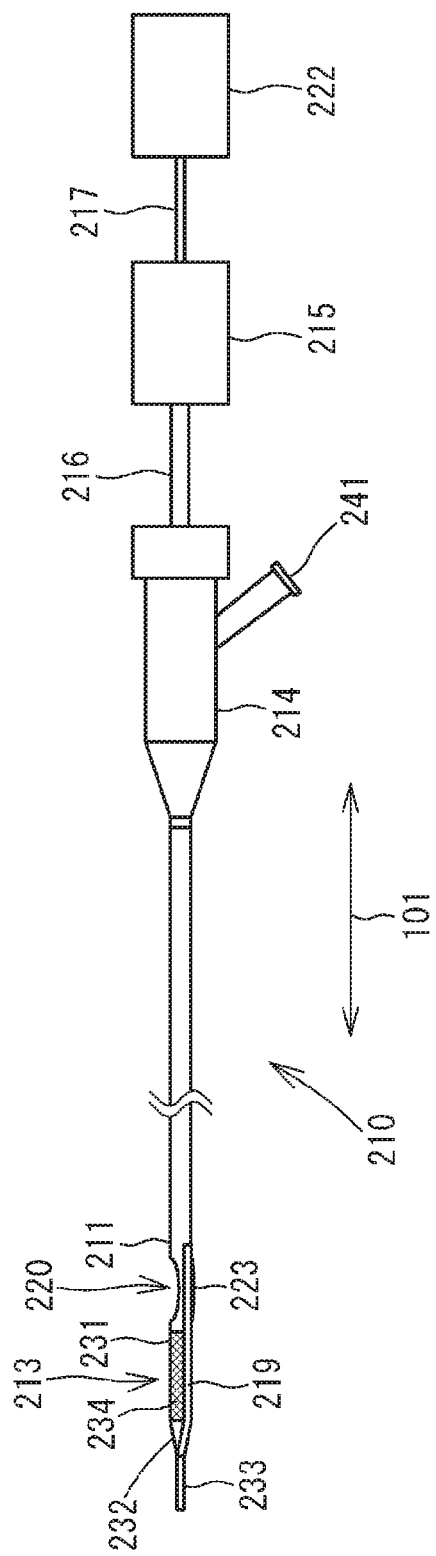
FIG. 7 is a view illustrating the external configuration of a catheter 210 in a state where a balloon 223 is contracted.
Figure 8:
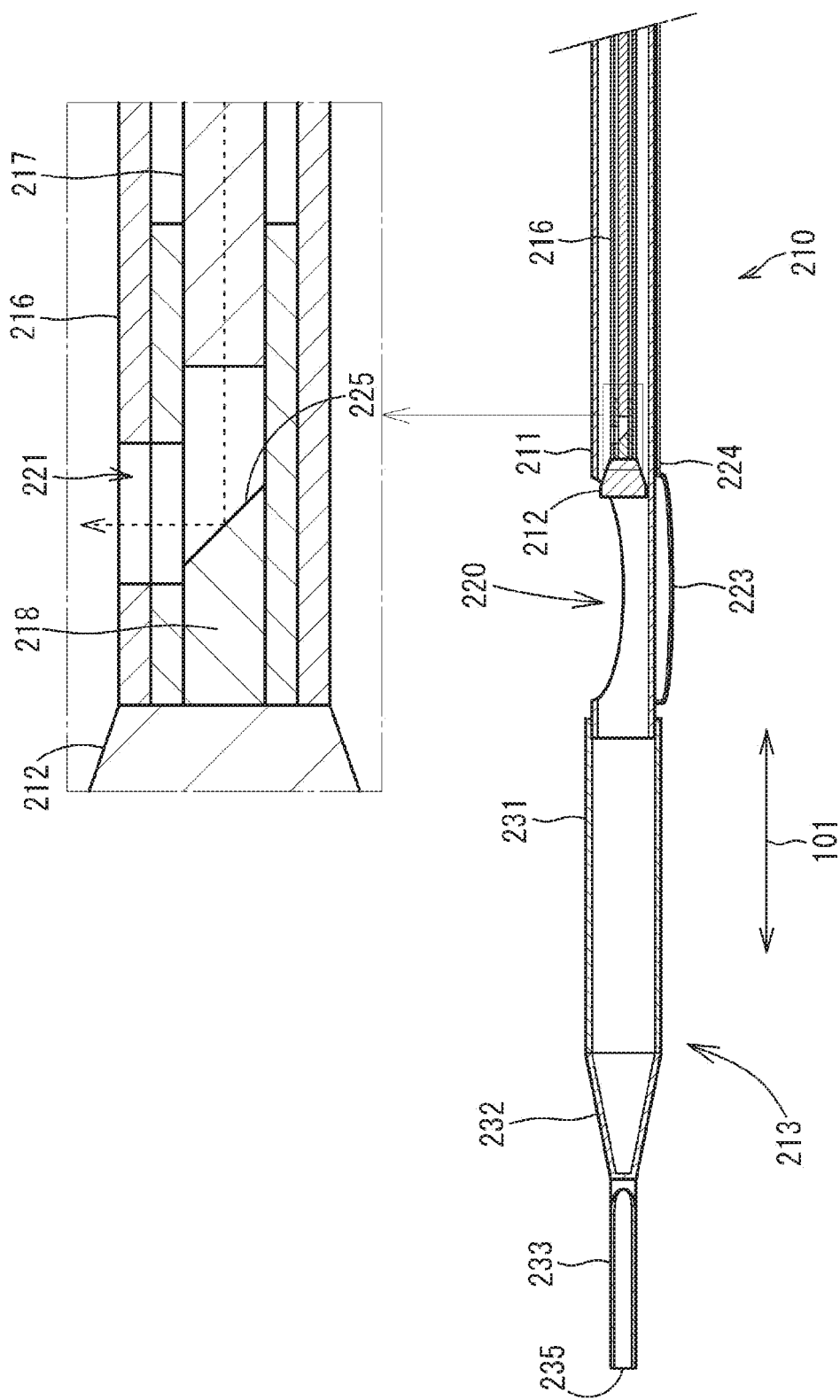
FIG. 8 is an enlarged cross sectional view illustrating the internal configuration in the vicinity of a distal end portion 213 of the catheter 210.

As illustrated in FIGS. 7 and 8, a catheter 210 has a shaft 211 (which is equivalent to the tube body), a torque shaft 216 and a cutter 212 provided in the shaft 211, a distal end portion 213 configuring the distal end of the shaft 211, a proximal end portion 214 connected to the proximal end of the shaft 211, an actuator 215 which gives rotation to the cutter 212, an OCT image wire 217 (which is equivalent to the light guide material) and a reflective material 218 provided in the torque shaft 216, and a guide wire tube 219. The catheter 210 is used as a medical instrument which is inserted into a blood vessel to excise an atheroma or photographs ultrasonic images of a blood vessel.

The shaft 211 is a tube capable of containing the cutter 212 thereinside. The shaft 211 is configured from a surgical stainless steel circular tube or a synthetic resin circular tube, for example, and has flexibility which allows the shaft 211 to be elastically curved corresponding to the curved shape of a blood vessel. The distal end and the proximal end of the shaft 211 each are opened. The outer diameter of the shaft 211 is set according to the inner diameter of a blood vessel into which the shaft 211 is to be inserted, e.g., coronary arteries. The inner diameter of the shaft 211 is set according to the outer diameter of the cutter 212. The outer diameter and the inner diameter of the shaft 211 are almost uniform over the axial direction 101 of the shaft 211. The length in the axial direction 101 of the shaft 211 is set in consideration of the length from catheter insertion portions, such as the human limbs, to the affected portion.

As illustrated in FIG. 8, an opening 220 is formed in the vicinity of the distal end portion 213 in the shaft 211. The opening 220 is formed by cutting out a part of the side wall of the shaft 211. The shape and the size of the opening 220 are set in consideration of the shape and the size of an atheroma which is probably formed in the affected portion.

As illustrated in FIG. 8, the cutter 212 is provided in the vicinity of the opening 220 in the internal space of the shaft 211. The cutter 212 has an approximately cylindrical shape and the outer diameter is a little smaller than the inner diameter of the shaft 211. Therefore, the cutter 212 can move along the axial direction 101 in the internal space of the shaft 211. On the distal end side of the cutter 212, a plurality of blades are formed in such a manner as to radially extend from the center. Although not illustrated in FIG. 8, a through-hole is formed along the axial direction 101 in the center of the cutter 212.

The torque shaft 216 is inserted into and passed through the internal space of the shaft 211. The distal end side thereof is connected to the cutter 212, and the proximal end side thereof is extended to the outside of the proximal end portion 214 of the shaft 211. The torque shaft 216 has flexibility which allows the torque shaft 216 to be elastically curved corresponding to the curved shape of a blood vessel together with the shaft 211 and has torsional rigidity which transmits rotation around the axial direction 101. The torque shaft 216 is configured to form a tube shape as a whole by continuing surgical stainless steel in a spiral shape, for example.

As illustrated in FIG. 7, the torque shaft 216 is connected to the actuator 215. Due to the fact that the torque shaft 216 receives drive transmitted from the actuator 215 to rotate, the cutter 212 rotates. Due to the fact that the torque shaft 216 is moved in the axial direction 101, the cutter 212 moves in the axial direction 101 in the internal space of the shaft 211.

As illustrated in FIG. 8, an opening 221 is formed in the vicinity of the distal end connected to the cutter 212 in the torque shaft 216. The opening 221 is formed by cutting out a part of the side wall of the torque shaft 216. The shape and the size of the opening 221 are set in consideration of the shape and the size of near-infrared rays which are reflected by the reflective material 218 to be emitted in a direction orthogonal to the axial direction 101.

As illustrated in FIG. 8, an OCT image wire 217 is inserted into and passed through the internal space of the torque shaft 216 from the proximal end portion 214 to be extended to the opening 221. The inner diameter of the internal space of the torque shaft 216 is equivalent to the outer diameter of the OCT image wire 217. Therefore, the axis of the OCT image wire 217 and the axis of the torque shaft 216 are almost in agreement with each other. Although not illustrated in detail in each figure, the OCT image wire 217 is one in which an optical fiber is built in a transparent outer casing and which is provided with a lens emitting near-infrared rays on a distal end portion. The near-infrared rays emitted from the lens are emitted along the axial direction of the OCT image wire 217. The OCT image wire 217 propagates near-infrared rays to be supplied from a light source built in an OCT body display portion 222 to the distal end side.

In the internal space of the torque shaft 216, the reflective material 218 is disposed facing the distal end of the OCT image wire 217 in the axial direction 101. In the reflective material 218, a reflective surface 225 facing the distal end of the OCT image wire 217 is a surface inclined to form an angle of 45° with respect to the axis of the OCT image wire 217. The reflective surface 225 is exposed to the outside of the torque shaft 216 through the opening 221 of the torque shaft 216. The reflective material 218 is a columnar body containing an optical fiber, resin, or the like. The outer diameter thereof is equivalent to the inner diameter of the internal space of the torque shaft 216. Therefore, the axis of the reflective material 218 and the axis of the torque shaft 216 are almost in agreement with each other. On a surface including the reflective surface 225 of the reflective material 218, metal layers are laminated. The metal layer is formed by, for example, plating or sputtering nickel, gold, aluminum, chromium, and the like alone or a mixture thereof onto the surface of the reflective material 218. By the reflective surface 225, near-infrared rays emitted along the axial direction 101 from the OCT image wire 217 are reflected in a direction (second direction) orthogonal to the axial direction 101 to be emitted to the outside of the torque shaft 216 through the opening 221. The angle of the reflective surface 225 with respect to the axis of the OCT image wire 217 is an example and may not necessarily be 45°. More specifically, the near-infrared rays to be emitted along the axial direction 101 from the OCT image wire 217 may be reflected in a direction crossing the axial direction 101.

The OCT image wire 217 and the reflective material 218 can rotate around the axis (axial direction 101) integrally with the torque shaft 216 and can slide in the axial direction 101 in a state of holding the mutual positional relationship, i.e., the clearance and the angle of the reflective surface 225. The rotation and the slide of the OCT image wire 217 and the reflective material 218 are controlled by directly or indirectly operating the proximal end side of the torque shaft 216 extended from the proximal end portion 214. Specifically, driving force from the actuator 215 is given to the proximal end side of the torque shaft 216, whereby the torque shaft 216 is rotated and slid.

As illustrated in FIGS. 7 and 8, a balloon 223 is provided at a position opposite to the opening 220 with respect to the axis of the shaft 211. The balloon 223 can outwardly expand from the side wall of the shaft 211 and is folded and stuck to the side wall of the shaft 211 until the catheter 210 is inserted into a blood vessel. As raw materials of the balloon 223, materials having biocompatibility are preferable. Specific examples of the materials include polyurethane, polyethylene, polyester, polypropylene, polyamide, polyamide elastomer, polytetrafluoroethylene, polyvinylidene fluoride, and the like.

As illustrated in FIG. 8, the proximal end side of the balloon 223 is connected to a tube for balloon 224 provided along the side wall of the shaft 211. The internal space of the tube for balloon 224 is caused to communicate with the internal space of the balloon 223. The tube for balloon 224 is extended to the proximal end portion 214 and the internal space of the tube for balloon 224 is connected to a port 241 of the proximal end portion 214. Due to the fact that liquid, such as physiological saline, injected from the port 241 of the proximal end portion 214 flows into the balloon 223, the balloon 223 is expanded in a blood vessel. The tube for balloon 224 is a molded body of flexible plastic which can be elastically deformed, such as polyamide, polyamide elastomer, and polyetheramide.

As illustrated in FIGS. 7 and 8, the distal end portion 213 is connected to the distal end of the shaft 211. As illustrated in FIG. 8, the distal end portion 213 has a blade tube 231, a reduced diameter portion 232, and a distal end tip 233.

As illustrated in FIGS. 7 and 8, the blade tube 231 is a circular tube in which both sides are opened. The blade tube 231 is connected to the distal end of the shaft 211 and the internal space thereof is caused to communicate with the internal space of the shaft 211. The blade tube 231 is one in which flexible plastic which can be elastically deformed, such as polyamide, polyamide elastomer, and polyetheramide, is reinforced with a core material 234. The core material 234 is embedded in the side wall of the blade tube 231. The core material 234 is formed into a cylindrical shape by braiding wire rods, such as surgical stainless steel, into a mesh. The inner diameter of the blade tube 231 is almost equal to the outer diameter of the shaft 211 and the blade tube 231 is fitted to the distal end of the shaft 211 from the outside. The outer diameter and the inner diameter of the blade tube 231 are almost uniform over the axial direction 101. In each figure other than FIG. 7, the core material 234 is not illustrated.

As illustrated in FIGS. 7 and 8, the reduced diameter portion 232 is a circular tube in which the blade tube 231 side is opened and the outer diameter decreases toward the distal end in a tapered shape. The reduced diameter portion 232 is connected to the distal end of the blade tube 231 and the internal space thereof is caused to communicate with the internal space of the blade tube 231. The reduced diameter portion 232 contains flexible plastic which can be elastically deformed, such as polyamide and polyetheramide. The inner diameter on the proximal end side of the reduced diameter portion 232 is almost equal to the outer diameter of the distal end of the blade tube 231. The reduced diameter portion 232 is fitted to the distal end of the blade tube 231 from the outside, and then thermally fused thereto. The distal end side of the reduced diameter portion 232 is sealed. The thickness decreases toward the distal end side on the distal end side of the reduced diameter portion 232.

As illustrated in FIGS. 7 and 8, the distal end tip 233 is connected to the distal end of the reduced diameter portion 232. A distal end 235 of the distal end tip 233 is projected from the distal end of the reduced diameter portion 232 to the outside in the axial direction 101. The distal end tip 233 contains flexible plastic which can be elastically deformed, such as polyamide and polyetheramide. The distal end tip 233 is thermally fused on the distal end side of the reduced diameter portion 232. On the distal end of the distal end tip 233, a marker which can be confirmed by X-rays or the like may be provided.

As illustrated in FIG. 7, a guide wire tube 219 is provided over the distal end tip 233, the blade tube 231, and a part of the distal end side of the shaft 211 along the outer peripheral surface of each of the distal end tip 233, the blade tube 231, and the distal end of the shaft 211. The guide wire tube 219 is a molded body of flexible plastic which can be elastically deformed, such as polyamide, polyamide elastomer, and polyetheramide. The guide wire tube 219 is disposed at a position where the guide wire tube 219 is not overlapped with the opening 220 of the shaft 211 and the balloon 223, e.g., in the vicinity of the boundary between the shaft 211 and the balloon 223. The internal space of the guide wire tube 219 is a guide wire lumen, and a guide wire which is not illustrated is inserted into and passed through the guide wire lumen.

The proximal end portion 214 is provided on the proximal end of the shaft 211. The proximal end portion 214 is a cylindrical member having an internal space continuing to the internal space of the shaft 211. The proximal end portion 214 is a molded body of resin, such as polypropylene or ABS. The proximal end portion 214 may serve as a handle in an operation of inserting and removing the shaft 211 into/from a blood vessel.

The proximal end portion 214 is provided with the port 241 extended in a direction crossing the axial direction 101. Another device, such as a syringe, is connected to the port 241, and then fluid, such as physiological saline, which is flown in and out from the device, flows in and out of the tube for balloon 224 from the proximal end portion 214. The proximal end portion 214 may be provided with another port continuing to the internal space of the shaft 211. Such a port is used for the purpose of, for example, collecting an excised atheroma entering the inside of the shaft 211.

From an opening on the proximal end side of the proximal end portion 214, the torque shaft 216 is extended. The actuator 215 is connected to the torque shaft 216. In the actuator 215, a motor, a battery, and the like are built. To the torque shaft 216, rotation of the motor of the actuator 215 is transmitted.

The OCT image wire 217 disposed in the internal space of the torque shaft 216 is connected to the OCT body display portion 222 through the actuator 215. The OCT body display portion 222 has a light source which supplies near-infrared rays, an interferometer, a portable reference mirror, a monitor, an arithmetic unit, and the like. Near-infrared rays supplied from the light source are split by the interferometer to be supplied to each of the OCT image wire 217 and the portable reference mirror. Then, near-infrared rays reflected in a blood vessel and near-infrared rays reflected on the portable reference mirror are combined in the interferometer. Interference signals of the near-infrared rays are treated by the arithmetic unit to be displayed as tomographic images of the blood vessel on a monitor.

[Usage Directions for Catheter 210]

Hereinafter, the usage directions for the catheter 210 are described with reference to FIGS. 9 and 10.

The catheter 210 is used when excising an atheroma 51 formed in the inner wall of a blood vessel 50. The position of the atheroma 51 is confirmed by the blood vessel tomographic images by the OCT. The catheter 210 is inserted into the blood vessel 50 from the distal end portion 213 in the state (FIG. 7) where the balloon 223 is contracted. Although not illustrated in each figure, a guide wire is inserted into the blood vessel 50 beforehand in the insertion of the catheter 210 into the blood vessel 50. The insertion of the guide wire into the blood vessel 50 is performed by a known technique. The catheter 210 is inserted into the blood vessel 50 from the distal end portion 213 while inserting the guide wire inserted into the blood vessel 50 into a guide wire tube 219.

The distal end portion 213 is advanced to the atheroma 51 in the blood vessel 50 while being elastically curved along the guide wire at a portion where the blood vessel 50 is curved, such as coronary arteries. When the distal end portion 213 reaches the atheroma 51, and the opening 220 of the shaft 211 faces the atheroma 51, the insertion of the shaft 211 into the blood vessel 50 is ended. By rotating the torque shaft 216 by the actuator 215 and supplying near-infrared rays to the OCT image wire 217 from the OCT body display portion 222, tomographic images of the blood vessel 50 are displayed in the OCT body display portion 222. By confirming the tomographic images of the blood vessel 50, it can be confirmed that the opening 220 has reached the position corresponding to the atheroma 51 and the state of the atheroma 51 can be confirmed. Thereafter, the guide wire is drawn out of the proximal end portion 214 side of the catheter 210. The actuator 215 is connected to the torque shaft 216 of the cutter 212. In FIGS. 9 and 10, the guide wire is omitted.

Figure 9:
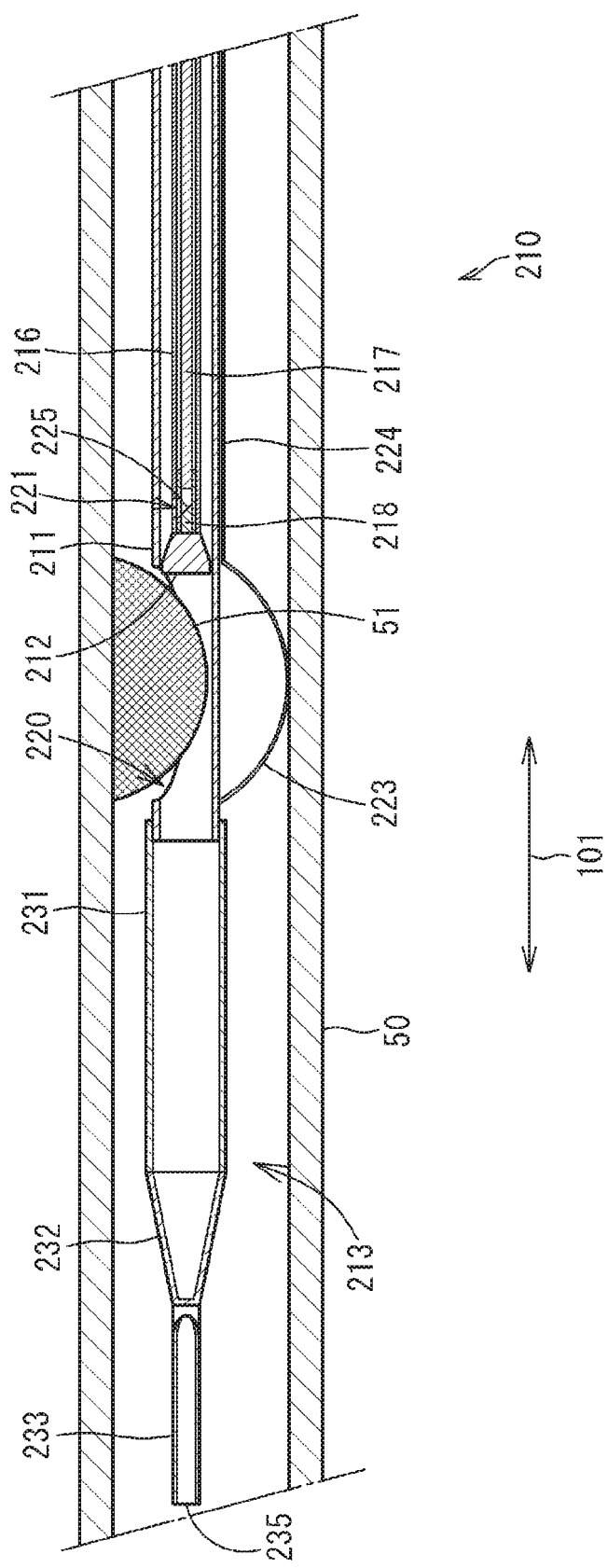
FIG. 9 is a schematic view illustrating a state where the balloon 223 is expanded in the blood vessel 50.
Figure 10:
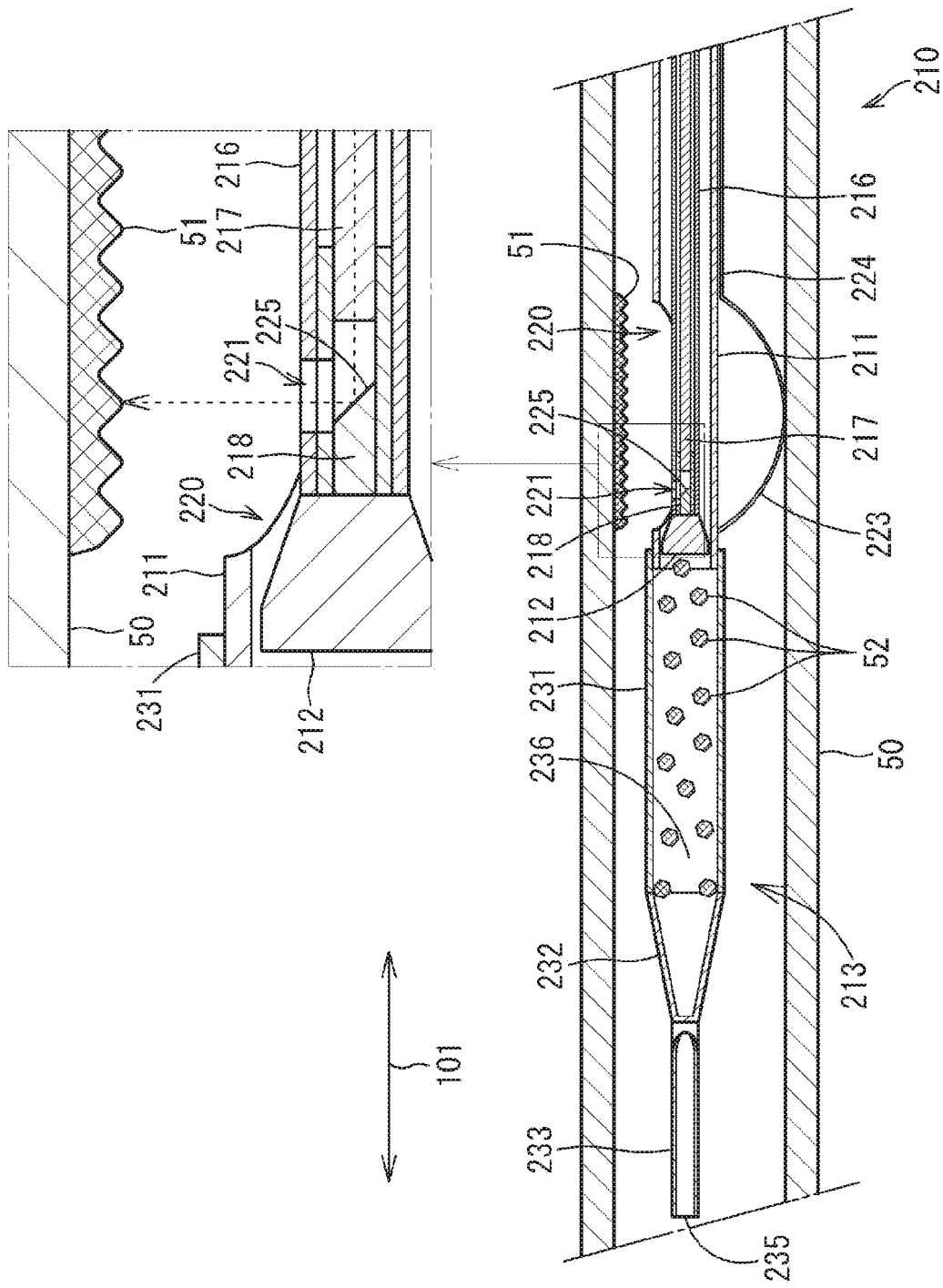
FIG. 10 is a schematic view illustrating the state where the atheroma 51 is excised in the blood vessel 50.

In the state where the opening 220 of the shaft 211 faces the atheroma 51 as illustrated in FIG. 9, the balloon 223 in the contracted state is expanded by fluid which is caused to flow into the tube for balloon 224 from the port 241. When the expanded balloon 223 abuts on the inner wall of the blood vessel 50 on a side opposite to the atheroma 51, the opening 220 is stuck to the atheroma 51, so that the atheroma 51 partially enters the internal space of the shaft 211 from the opening 220. In the state above, the catheter 210 is fixed to the blood vessel 50.

Subsequently, the rotation of the actuator 215 is transmitted to the cutter 212 through the torque shaft 216 of the cutter 212, so that the cutter 212 is rotated. Due to the fact that the torque shaft 216 is advanced to the distal end side in the axial direction 10 with respect to the shaft 211 on the proximal end portion 214 side, the rotating cutter 212 abuts on the atheroma 51, so that the atheroma 51 is excised by the cutter 212. Fragments 52 of the excised atheroma 51 enter the internal space of the blade tube 231 through the internal space of the shaft 211.

After the atheroma 51 is excised by the cutter 212, tomographic images of the blood vessel 50 in the state where the atheroma 51 is excised can be obtained by the same OCT as above. Thus, the state where the atheroma 51 is excised can be immediately confirmed, i.e., without drawing out the catheter 210 from the blood vessel 50. Therefore, when the excision of the atheroma 51 is insufficient, for example, the remaining atheroma 51 can be excised by rotating the cutter 212. The collection of the tomographic images of the blood vessel 50 may be performed while moving the reflective material 218 together with the torque shaft 216 in the axial direction 101 with respect to the shaft 211. Thus, the tomographic images continuing in the length direction (which is almost in agreement with the axial direction 101) of the blood vessel 50 can be obtained. Then, when the excision of the atheroma 51 is completed, the balloon 223 is contracted, and then the catheter 210 is drawn out of the blood vessel 50 to be collected.

Operational Effects of Second Embodiment

According to the catheter 210 of the second embodiment, the atheroma 51 in the blood vessel 50 can be excised and the ultrasonic images of the blood vessel 50 can be obtained by the simple structure.

Moreover, since the OCT image wire 217 and the reflective material 218 are disposed in the internal space of the torque shaft 216, near-infrared rays can be guided to the vicinity of the atheroma 51 in the blood vessel 50 to be reflected in the torque shaft 216.

Moreover, since the OCT image wire 217 and the reflective material 218 can be rotated integrally with the torque shaft 216, the excision of the atheroma 51 and the OCT can be realized by controlling the number of rotations of the motor in the actuator 215.

Moreover, since the OCT image wire 217 and the reflective material 218 can move along the axial direction 101 integrally with the torque shaft 216, tomographic images of the blood vessel 50 along the axial direction 101 can be obtained.

Moreover, since the OCT image wire 217 and the reflective material 218 are disposed in the internal space of the torque shaft 216, the OCT image wire 217 and the reflective material 218 are covered with the torque shaft 216 to be protected.

Moreover, since the guide wire tube 219 is provided along the shaft 211, the catheter 210 can be inserted into the blood vessel 50 along a guide wire.

[Modification]

In the embodiments described above, although the guide wire tube 219 has a so-called rapid exchange type structure in which the guide wire tube 219 is disposed on the outside of the shaft 211. However, as illustrated in FIG. 11, a so-called over-the-wire type structure in which the internal space of the torque shaft 216 is used as a guide wire lumen may be adopted.

Figure 11:
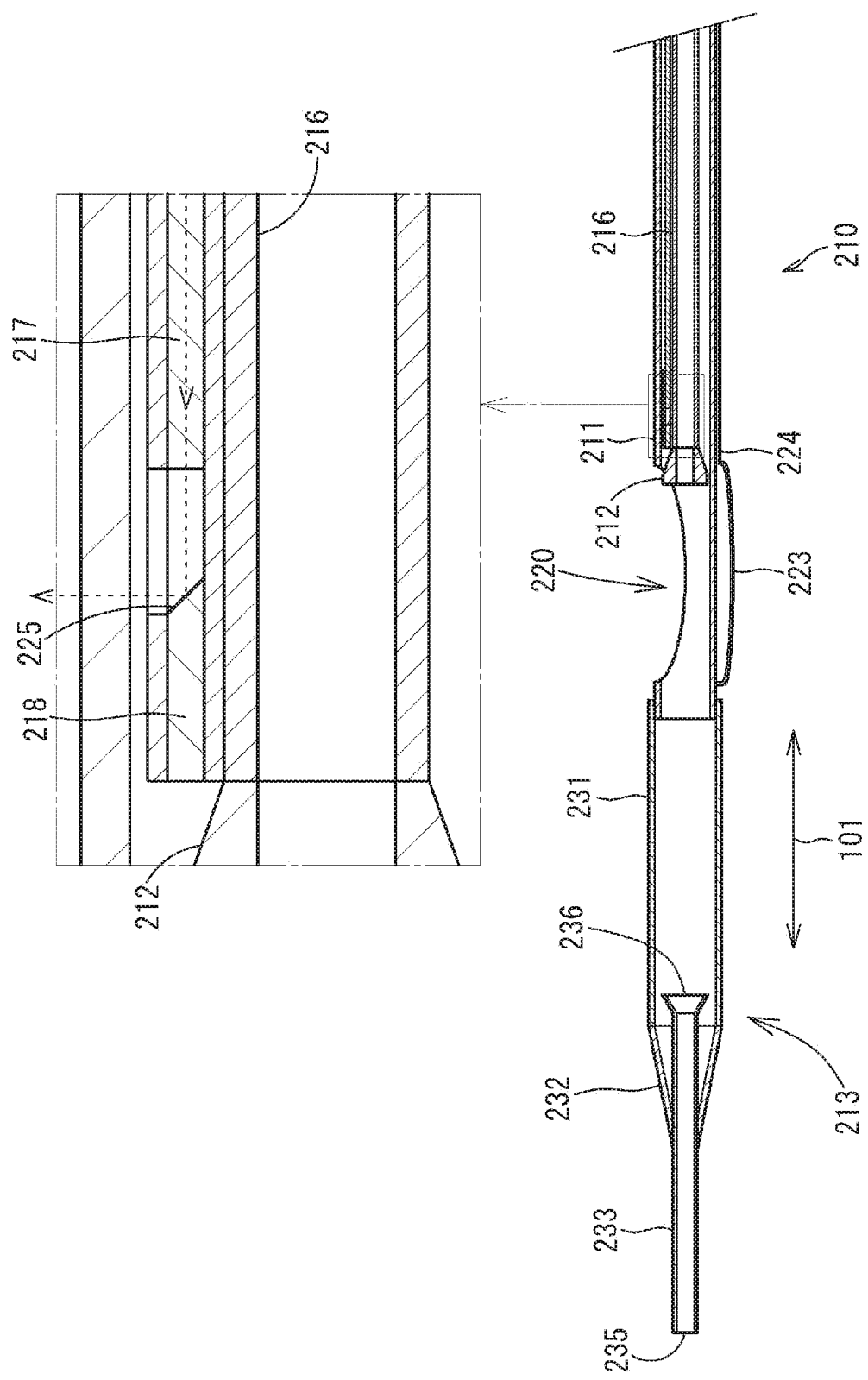
FIG. 11 is an enlarged cross sectional view illustrating a modification of the catheter 210.

When the over-the-wire type structure is adopted, the OCT image wire 217 and the reflective material 218 are disposed in such a manner as to face each other with respect to the axial direction 101 along the outer peripheral surface of the torque shaft 216 as illustrated in FIG. 11. Near-infrared rays to be emitted along the axial direction 101 from the OCT image wire 217 are reflected by the reflective material 218 in a direction (direction orthogonal to) crossing the axial direction 101 toward the outside of the torque shaft 216. Thus, the near-infrared rays are not emitted to the guide wire inserted into and passed through the internal space of the torque shaft 216. In the over-the-wire type structure, the opening 221 does not need to be formed in the torque shaft 216.

When the over-the-wire type structure is adopted, a circular tube, in which both sides are opened and the outer diameter of a proximal end 236 side increases in a tapered shape as illustrated in FIG. 11 is adopted as the distal end tip 233. The distal end tip 233 is connected to the distal end of the reduced diameter portion 232 and the internal space thereof is caused to communicate with the internal space of the reduced diameter portion 232. A distal end 235 of the distal end tip 233 is projected from the distal end of the reduced diameter portion 232 to the outside in the axial direction 101. The proximal end 236 side of the distal end tip 233 is extended in the axial direction 101 in the internal space of the reduced diameter portion 232 and the proximal end 236 reaches the internal space of the blade tube 231. More specifically, a portion including a distal end side portion of the blade tube 231 and the reduced diameter portion 232 has a double tube structure in which the blade tube 231 and the reduced diameter portion 232 serve as the outer side and the distal end tip 233 serves as the inner side.

Although the diameter of the distal end tip 233 is increased on the proximal end 236 side, the other outer diameter and the inner diameter of the other portion are almost uniform. The outer diameter of the uniform portion is smaller than the inner diameter of the blade tube 231 and is almost equal to the inner diameter of the distal end of the reduced diameter portion 232. Although the diameter of the proximal end 236 side is increased, the maximum diameter is smaller than the inner diameter of the blade tube 231.

A through-hole along the axial direction 101 is formed in the cutter 212. A guide wire lumen is formed along the axial direction 101 of the shaft 211 by the internal space of the torque shaft 216, the through-hole of the cutter 212, the internal space of the blade tube 231, and the internal space of the distal end tip 233.

The distal end surface of the OCT image wire 217 may be a surface inclined to form an angle of 45° with respect to the axial direction 101 and the reflective material 218 may be provided on the distal end surface. In that case, the reflective material 218 disposed at a position apart from the OCT image wire 217 is not present.

REFERENCE SIGNS LIST

10 Catheter
11 Shaft (Tube body)
12 Cutter
16 IVUS shaft (Outer tube body)
17 Ultrasound probe
20 Opening
23 Balloon
43 Notch portion
44 Support portion
210 Catheter
211 Shaft (Tube body)
212 Cutter
216 Torque shaft
217 OCT image wire (Light guide material)
218 Reflective material
219 Guide wire tube (Guide wire lumen)
220,221 Opening
223 Balloon

The invention claimed is:

1. A catheter comprising:
 a tube body having an opening in a part of a side wall on a distal end side;
 a torque shaft which is inserted into and passed through an internal space of the tube body;
 a light guide material extending along the torque shaft and emitting light along a first direction;
 a reflective material spaced from a distal end of the light guide material, wherein the reflective material reflects light emitted from the light guide material in a second direction transverse to the first direction;
 a cutter connected to the torque shaft within the internal space of the tube body such that the torque shaft transmits a rotation torque to the cutter, wherein the cutter is located distally of the reflective material and the light guide material; and
 a balloon which is disposed on a side opposite to the opening with respect to an axis of the tube body and outwardly expands from the side wall of the tube body, wherein:
  (a) an inner diameter of the internal space of the torque shaft is equivalent to an outer diameter of the light guide material,
  (b) the light guide material and the reflective material are disposed within the internal space of the torque shaft such that the light guide material and the reflective material have a common axial orientation, and
  (c) the light guide material and the reflective material can move integrally with the torque shaft along the first direction.

2. The catheter according to claim 1, wherein the reflective material emits light reflected in the second direction to an outside of the torque shaft through an opening formed in a side wall of the torque shaft.

3. A catheter comprising:
 a tube body having an opening in a part of a side wall on a distal end side;
 a torque shaft which is inserted into and passed through an internal space of the tube body;
 a light guide material extending along the torque shaft and emitting light along a first direction;
 a reflective material spaced from a distal end of the light guide material, wherein the reflective material reflects light emitted from the light guide material in a second direction transverse to the first direction;
 a cutter connected to the torque shaft within the internal space of the tube body such that the torque shaft transmits a rotation torque to the cutter, wherein the cutter is located distally of the reflective material and the light guide material; and
 a balloon which is disposed on a side opposite to the opening with respect to an axis of the tube body and outwardly expands from the side wall of the tube body wherein:

(a) the light guide material and the reflective material are disposed on an outer peripheral surface side of the torque shaft,
(b) the light guide material and the reflective material can move integrally with the torque shaft along the first direction,
(c) a through-hole is formed in the cutter along the first direction, and
(d) at least the through-hole formed in the cutter and an internal space of the torque shaft form a guide wire lumen.

* * * * *